United States Patent [19]

Hannah et al.

[11] 4,248,214
[45] Feb. 3, 1981

[54] ILLUMINATED URETHRAL CATHETER

[75] Inventors: Richard E. Hannah, Springrove, Ill.; Robert S. Kish, 211 W. Beaver Ave., State College, Pa. 16801

[73] Assignee: Robert S. Kish, State College, Pa.

[21] Appl. No.: 41,499

[22] Filed: May 22, 1979

Related U.S. Application Data

[63] Continuation-in-part of Ser. No. 849,092, Nov. 7, 1977, abandoned.

[51] Int. Cl.³ ............................ A61B 1/06; A61B 1/30
[52] U.S. Cl. .................................... 128/7; 128/349 R; 128/23
[58] Field of Search ......................... 128/3–8, 128/303.1, 303.15, 303.11, 395–397, 348, 349 R, 275, 275.1, 23, 11, 350 R

[56] References Cited

U.S. PATENT DOCUMENTS

| 1,642,187 | 9/1927 | Young | 128/397 |
|---|---|---|---|
| 1,704,764 | 3/1929 | Schellberg | 128/6 |
| 1,747,407 | 2/1930 | Wappler | 128/6 |
| 1,767,267 | 6/1930 | Wappler | 128/349 R |
| 1,800,277 | 4/1931 | Boerstler | 128/397 |
| 1,939,413 | 12/1933 | Robinson | 128/395 |
| 2,235,979 | 3/1941 | Brown | 128/6 |
| 2,699,770 | 1/1955 | Fourestier et al. | 128/6 |
| 2,793,639 | 5/1957 | Roberge | 128/6 |
| 3,051,176 | 8/1962 | Alberti | 128/276 |
| 3,131,690 | 5/1964 | Innis et al. | 128/6 |
| 3,261,356 | 7/1966 | Wallace | 128/276 |
| 3,760,797 | 9/1973 | Stauffer | 128/6 |
| 3,771,516 | 11/1973 | Corriero | 128/23 |
| 3,835,842 | 9/1974 | Iglesias | 128/7 |
| 3,886,933 | 6/1975 | Mori et al. | 128/7 |
| 3,900,022 | 8/1975 | Widran | 128/7 |

FOREIGN PATENT DOCUMENTS

| 636381 | 3/1962 | Italy | 128/6 |
|---|---|---|---|
| 1042874 | 9/1966 | United Kingdom | 128/6 |

Primary Examiner—William E. Kamm
Assistant Examiner—Arthur S. Rose
Attorney, Agent, or Firm—Thomas Hooker

[57] ABSTRACT

A urethral catheter includes a flexible transparent catheter tube, a drainage adapter having a major aperature secured to the proximal end of the catheter tube, a minor aperature axially aligned with the major aperature and a drainage funnel located between the aperatures and a fiber optic member having means on one end for attachment to a light source and a flexible fiber optic strand on the other end thereof extending through the minor and major aperatures and through the interior lumen of the tube with the distal end located adjacent the distal end of the tube. An end portion of the fiber optic within the tube is abraded to provide circumferential illumination extending outwardly of the fiber optic end through the transparent tube. The fiber optic may be axially adjusted within the tube by means of the sliding fit with the minor aperature of the drainage adapter.

10 Claims, 7 Drawing Figures

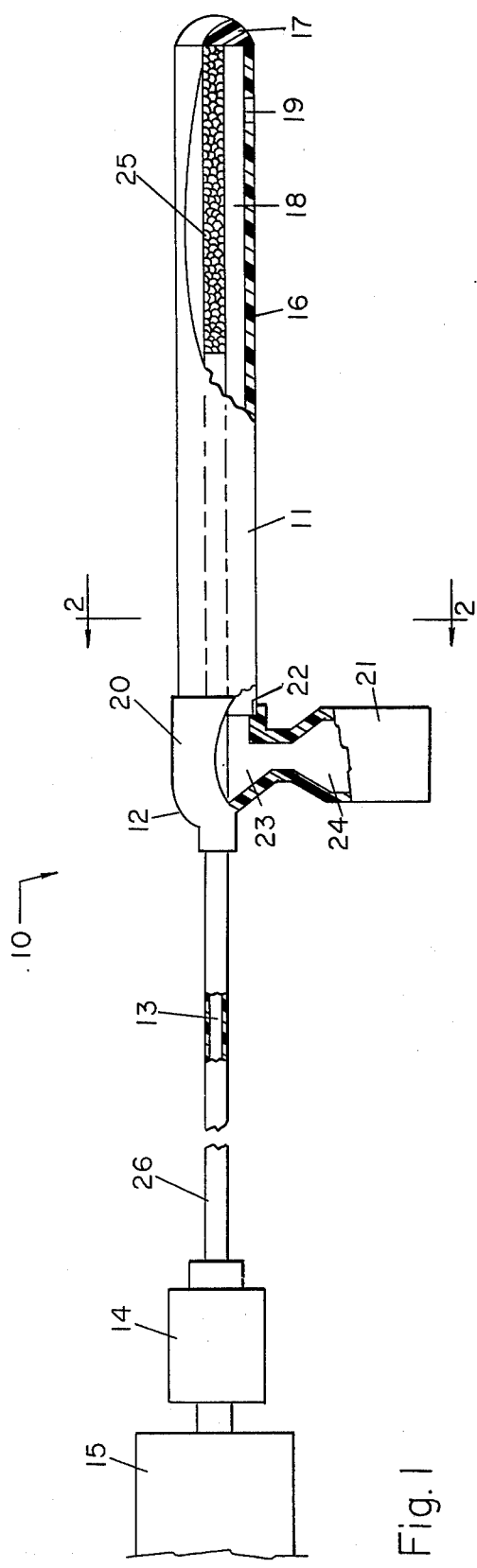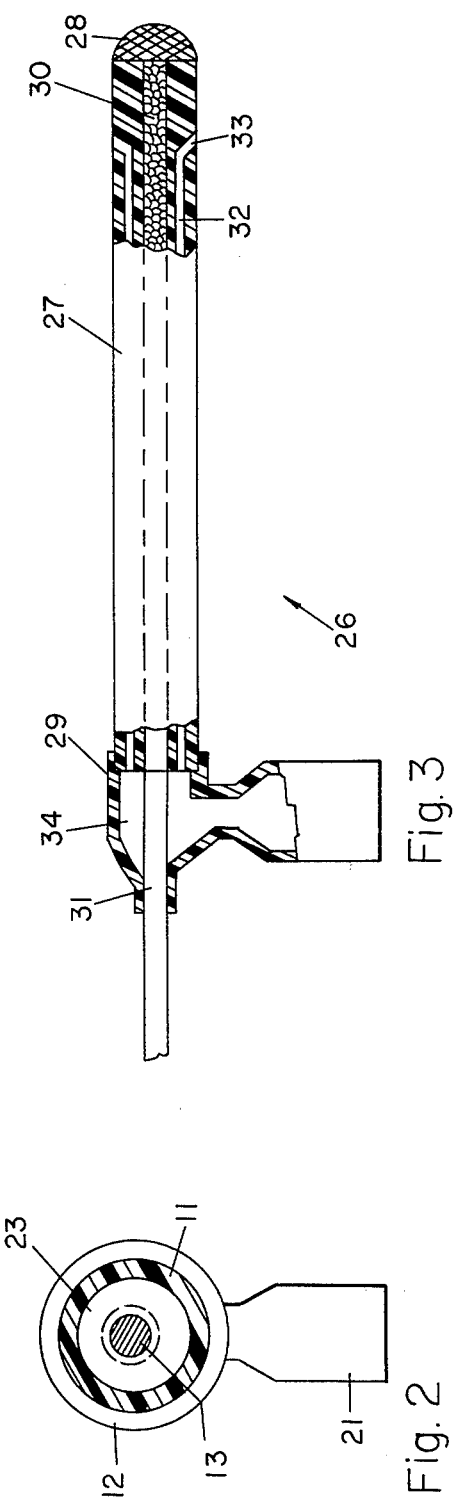

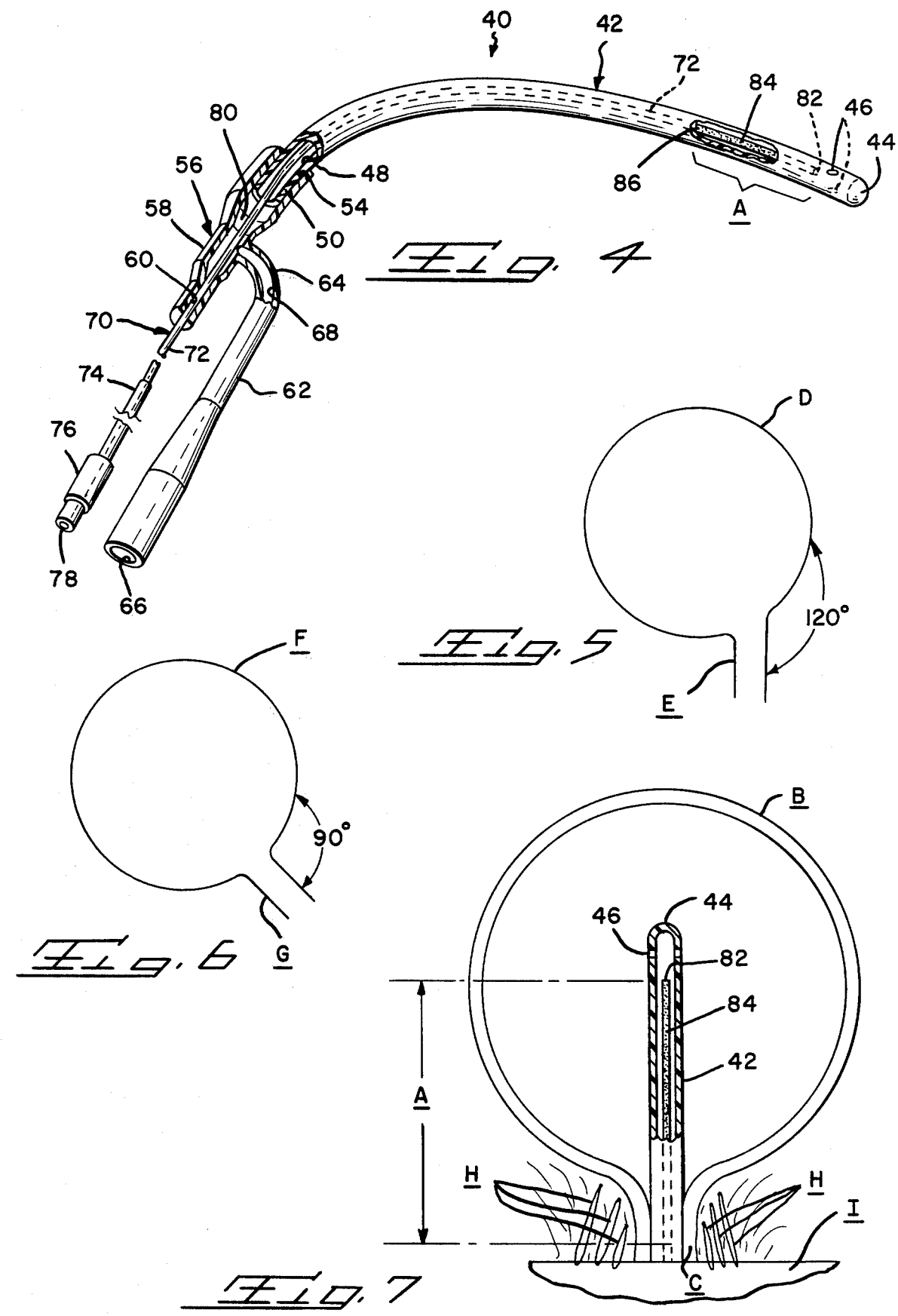

ILLUMINATED URETHRAL CATHETER

This application is a continuation-in-part of our co-pending United States application Serial No. 849,092 filed Nov. 7, 1977, now abandoned.

This invention relates to an improved illuminated catheter device primarily intended as a urethral catheter for draining the urinary bladder while providing circumferential cold illumination of the adjacent urinary tract. Such illumination enables the surgeon to accurately locate the bladder, junction and urethra without distorting the same so that, for instance, support sutures may be accurately placed adjacent the urethrovesical junction without injury to the urinary tract.

Conventionally, the urethrovesical junction has been located using endoscopy, cystotomy or traction of an inflated urinary catheter with manual palpation of the vesical neck. These procedures are inherently inefficient since they distort the urinary tract and are capable of injuring the tract if misused, thereby increasing immediate or delayed surgical morbidity.

The prior art includes a number of catheters with specific illuminating features, particularly of the endoscopic and cystoscopic type where an image is conveyed along the instrument to a viewing location at the proximal end. For instance, Alberti U.S. Pat. No. 3,051,176 discloses a rigid rectoscope with a hot lamp and an angularly oriented viewing field positioned within a rigid bulb having fluid ingress and egress openings.

Wallace U.S. Pat. No. 3,261,356 discloses a rigid suction device having a curved central lumen with a cylindrical fiber optic member surrounding the lumen and terminating at the distal end to enable the surgeon to see to position the suction end of the lumen during an operative procedure.

The flexible Foley catheter is well known in the art and comprise a thin flexible tube having a sealed end with inlet eyelets adjacent the end to permit ingress of fluids desired to be removed from a body cavity.

The improved illuminated urethral catheter of the present invention is particularly adapted for insertion through the urethra and into the bladder of a patient and includes flexible transparent tube with a drainage lumen communicating with the bladder to enable urine to be removed during a surgical procedure and a central fiber optic member having a light emitting end portion adjustable along the length of the catheter so that it may be positioned partially within the urethra and partially within the bladder. The end portion provides a circumferential source of cold light sufficient to illuminate the surface of the bladder, the urethrovesical junction, and the urethra. The light-emitting portion of the fiber optic emits a greater intensity of light at the proximal end than at the distal end, thereby providing required high intensity illumination to enable the surgeon to locate the urethra and the urethra-bladder junction. The light emitted from the distal end of the fiber optic, although less than the proximal end thereof, is sufficient to illuminate the walls of the bladder. The exterior diameter of the catheter preferably has a snug sliding fit with the interior wall of the urethra so that it is held in place during adjustment of the fiber optic member to move the light emitting portion to the required location for proper surgical illumination.

The illuminated urethra catheter includes a catheter tube, a fiber optic member and a drainage adapter secured to the distal end of the tube with axially aligned major and minor aperatures. The proximal end of the tube extends into the major aperature and forms a fluid tight joint therewith. The fiber optic member extends through the minor aperature and into the tube with the distal end of the fiber optic member located adjacent the distal end of the tube. A drainage funnel extends away from the drainage adapter between the aperatures. In one embodiment of the invention this drainage funnel is bent with respect to the adapter and generally parallels the axis of the fiber optic member, thereby facilitating location of a collection receptacle remote from the incision.

Light emanates outwardly of the distal end of the fiber optic member 360° around its circumference to assure a uniform circumferential illumination is provided. In this way, it is not necessary to orient the fiber optic angularly within the catheter in order to provide desired cold illumination of the urinary tract. The catheter is simply inserted through the urethra so the distal end thereof is within the bladder and the fiber optic is manually positioned to illuminate the desired portion of the tract. When the catheter is used while performing the Marshall-Marchetti-Kranz procedure on a female patient, the light-emitting end of the fiber optic is positioned partially within the bladder and partially within the urethra in order to provide illumination for the walls of the bladder, the urethrovesical junction and the urethra itself. Such illumination enables the surgeon to accurately locate primary suspension sutures at the junction without injury to the urinary tract.

Other objects and features of the invention will become apparent as the description proceeds, especially when taken in conjunction with the accompanying drawings illustrating the invention, of which there are two sheets.

IN THE DRAWINGS

FIG. 1 is a side view of the drainage and illumination catheter of the present invention showing the associated apparatus for use with the invention, and with portions broken away to reveal the interior detail of the catheter.

FIG. 2 is a cross-sectional end view of the drainage and illumination catheter, taken along the line 2—2 in FIG. 1 in the direction of the arrows.

FIG. 3 is a partial, side view of a second embodiment of a drainage and illumination catheter constructed in accordance with the present invention, with portions of the catheter being broken away to reveal the interior details thereof.

FIG. 4 is a plan view of a third embodiment of the invention with portions broken away.

FIGS. 5 and 6 are diagramatic views of a bladder illustrating different posterior urethrovesical angles.

FIG. 7 is a sectional diagramatic view illustrating the end of the illuminated urethral catheter inserted within a bladder for use in performing a Marshall-Marchett-Kranz procedure.

Referring now in particular to FIGS. 1 and 2, there is shown a drainage and illumination catheter apparatus 10 constructed in accordance with the present invention. Apparatus 10 comprises generally a catheter 11, a drainage adapter 12 and a fiber optic 13. Fiber optic 13 is connected through a light adapter 14 to a suitable light source, as will be more fully described below.

In the embodiment as shown in FIG. 1, catheter 11 comprises a transparent catheter tube 16 having sealed thereto at the distal end a tip 17. Catheter tube 16 defines an interior lumen 18. A pair of drainage eyelets such as 19, are defined by the catheter tube 16 near the distal end of catheter 11. The drainage eyelets, such as 19, provide a communication between the lumen 18 and the exterior of the catheter 11.

The proximal end of catheter tube 16 is sealingly joined to a drainage adapter 12. Drainage adapter 12 includes a main portion 20 within which the catheter tube 16 is received, and a drainage funnel 21 which is connectable to a suitable drainage receptacle. Drainage adapter 12 may be formed from a variety of materials, but is most suitably formed from a flexible and resilient material such as natural or synthetic rubber. The main portion 20 of drainage adapter 12 defines a circular opening within which the proximal end of catheter tube 16 is received. An annular shoulder 22 is positioned at a location recessed from the circular opening, and defines an abutment against which the catheter tube 16 is positioned upon insertion into the opening of the main portion 20. The opening of drainage adapter 12 is preferably sized to be normally smaller than the catheter tube 16 such that the material defining the opening is stretched to receive the catheter tube 16. As a result, the catheter tube 16 is frictionally engaged and held by the drainage adapter.

The main portion 20 of drainage adapter 12 defines an interior chamber 23 which communicates with interior 24 of drainage funnel 21. Drainage funnel 21 is preferably shaped and sized to be useful in connection with standard drainage equipment, and preferably comprises a natural or synthetic rubber material for such application, as is known in the art.

As previously described, catheter tube 16 defines an interior lumen 18 which communicates through the drainage eyelets, such as 19, to the exterior of the catheter 11. As a result of the described construction of drainage adapter 12, the catheter 11 is suitable for providing drainage of fluid in the area outside of the catheter by passage of the fluid through the drainage eyelets, such as 19, lumen 18, interior chamber 23, and interior 24 of drainage funnel 21.

Received within lumen 18 of catheter tube 16 is a fiber optic 13. As shown in the embodiment of FIGS. 1 and 2, the fiber optic 13 preferably comprises a cylindrical member which extends to the distal end of catheter 11. Catheter tube 16 is sized to have a lumen 18 which is sufficiently larger than the fiber optic 13 to provide an annular passageway communicating between the drainage eyelets, such as 19, and the interior chamber 23 of drainage adapter 12.

Drainage adapter 12 further includes a circular aperture through which fiber optic 13 extends. The opening in drainage adapter 12 for reception of the fiber optic 13 is preferably sized to be normally smaller than the cross-sectional area of the fiber optic 13. As a result, the material defining the opening in the drainage adapter is stretched in order to receive the fiber optic 13, and thereby provides a tight, sealing fit with the fiber optic 13. The drainage adapter 12 thereby firmly retains the fiber optic 13 with respect to the drainage adapter and provides a sealing connection of the fiber optic with the drainage adapter.

Fiber optic 13 preferably extends through drainage adapter 12 and to the distal end of catheter 11. The distal end of fiber optic 13 may be secured to tip 17, but preferably is merely extended within lumen 18 to the distal end of catheter 11. Drainage eyelets such as 19, are then preferably sized to be smaller than the diameter of fiber optic 13, thereby preventing the fiber optic from extending through the drainage eyelets to the exterior of the catheter. Although the free, distal end of fiber optic 13 may rest against the interior wall of catheter 11, the provision of a plurality of drainage eyelets precludes the possibility of the fiber optic blocking all of the drainage eyelets and preventing drainage therethrough.

In accordance with known techniques, the distal portion of fiber optic 13 is scored or abraded at the surface to permit the light transmitted through the fiber optic to be emitted outwardly thereform. Most preferably the fiber optic 13 is abraded as previously described for a distance of approximately two inches adajacent the distal end of the fiber optic. This extent of abraded surface provides for sufficient and properly distributed illumination of the location of the catheter. As is generally known, the intensity of light transmitted through the abraded portion will decrease in the direction of the distal end, and a gradation of illumination will thereby be obtained by this construction. It will be appreciated that other illumination effects may be desirable depending upon the application of the catheter, and suitable variations in the amount and location of the abraded portion of the fiber optic should then be correspondingly made. The light transmitted through the abraded portion of the fiber optic 13 is thereafter transitted through the adjacent transparent portion of the catheter 11 to provide illumination of the location of the catheter.

In the embodiment of FIGS. 1 and 2, the entire catheter defining tube is transparent. However, the only requirement is that the portion of the catheter which surrounds the abraded portion of the fiber optic, and which is thereby required to transmit the light emitted by the fiber optic to the surrounding body tissue, is required to be transparent. The term "transparent", as used herein, is intended to mean that the material which defines that portion of the catheter must be of a type which will permit a sufficient amount of light to be transmitted therethrough to provide the required illumination of the body site. Therefore, the material properties will vary within readily determinable limits according to the area of the body in which the catheter is to be used. The intensity of light which is made available by the present invention will further depend upon the parameters for the light source 15, fiber optic 13, and amount of abraded portion 25.

Fiber optic 13 extends through an opening defined by the drainage adapter 12, and the proximal end of catheter 13 is received within a light adapter 14. Light adapter 14 may be constructed in accordance with known techniques, and functions to provide a connection of fiber optic 13 with light source 15. Light generated by light source 15 is thereby transmitted through light adapter 14 and fiber optic 13 to the catheter 11. Surrounding the fiber optic 13 for a distance between light adapter 14 and drainage adapter 12 is an outer sheath 26. Preferably the sheath extends for the full distance from light adapter 14 to the drainage adapter 12, although suitable results are obtained with a sheath which extends only about half the distance from the light adapter 15. Sheath 26 may be formed of any suitable material which will permit the required flexibility of fiber optic 13. The functions of the sheath 26 are to reduce the loss of light from the fiber optic through this distance and to protect the fiber optic from damage during use of the catheter. The sheath is most preferably adhesively bonded to the light adapter and suitably secured to the fiber optic. The length of the fiber optic between the light adapter 14 and drainage adapter 12 is preferably about five feet, since shorter lengths are generally inconvenient during use of the catheter, and greater lengths reduce the amount of light available at the distal end of the fiber optic. The fiber optic is preferably about 0.060 inches in diameter.

Referring now in particular to FIG. 3, there is shown a second embodiment 26 of a catheter apparatus constructed in accordance with the present invention. Apparatus 26 includes a catheter 27, tip 28 and drainage adapter 29. Apparatus 26 is substantially identical to apparatus 10 depicted in FIGS. 1 and 2. The primary difference in the apparatus 26 is that the catheter 27 defines several interior lumen. Catheter 27 defines a central lumen 30 within which the fiber optic 31 is received. Catheter 27 further defines drainage lumen, such as 32, which are separate from lumen 30 and communicate between the drainage eyelets, such as 33, and the interior 34 of drainage adapter 29. A further difference in the apparatus 26 is that the fiber optic 31 is shown without the protective sheath in the are adjacent the catheter 27. Although the embodiment of FIG. 3 is constructed in accordance with the present invention, the embodiment of FIG. 1 is preferred since it is more simply and economically produced.

FIG. 4 illustrates a third embodiment of the invention in which catheter apparatus 40 includes a flexible transparent catheter tube 42 with a sealed tip 44 at the distal end thereof and drainage openings or eyelets 46 extending through the side walls of tube 42 adjacent the tip. The openings 46 communicate the exterior environment adjacent the tip 44 with the interior drainage lumen 48 of the tube. The proximal end 50 of tube 42 is fitted within a major aperature 54 of resilient drainage adapter 56. The adapter 9 preferably formed from a flexible rubber material such as a natural latex. The major aperature 54 is formed with an interior diameter slightly less than the exterior diameter of tube 42 to provide a resilient fluid tight seal with the distal end of the tube thereby preventing leakage.

The adapter includes a main collecting portion 58 between the major aperature 54 and a minor aperature 60 on the end of the collecting portion 58 away from the major aperature. Aperatures 54 and 60 are axially aligned. A drainage funnel 62, integral with the main collecting portion 58 extends laterally from the collecting portion, through a bend 64 of approximately 90° and extends away from the major portion 54 in a direction generally parallel to the axis defined by the major and minor aperatures. The drainage funnel includes an expanded connection aperature 66 at its free end remote from the collecting portion 58 and an interior passage 68 communicating the interior of the main collecting portion with aperature 66.

The catheter apparatus 40 also includes a flexible fiber optic member 70 having an elongate flexible light transmitting fiber optic 72. The fiber optic 72 carries an outer protecting sheath 74 remote from the drainage adapter 56. A suitable mounting adapter 76 is affixed to the proximal end of the fiber optic member to facilitate attachment of the member to a high intensity light source (not illustrated) which transmits light into the exposed end 78 of the fiber optic. The fiber optic member 70 is sufficiently long to permit positioning of the light source remote from the catheter tube. The fiber optic 72 disclosed herein is formed from glass but may be formed from other suitable light conducting materials, such as a plastic material.

Fiber optic 72 extends through the minor aperature 60 of drainage adapter 56, through the interior collecting chamber 80 of portion 58 and into and along the interior lumen of the catheter tube 42 with the distal end 82 of the fiber optic located adjacent the sealed end 44 of the tube. The fiber optic and tube are both flexible so that both may be moved and deformed as desired during use of the device. The minor aperature 60 of the drainage adapter 56 has a tight sealing fit with the fiber optic 72 to form a liquid proof seal therebetween while permitting axial movement of the fiber optic relative to the adapter 56 and tube 42. In this way, the position of the end of the fiber optic within the tube may be altered as desired. Adjustment of the fiber optic within the tube is performed by grasping the end of the adapter adjacent aperature 60 and moving the fiber optic back or forth with respect to the adapter and tube. The fiber optic 72 is bared of the insulating sheath 74 a sufficient distance remote from the minor aperature to permit the described movement of the fiber optic within the tube as required.

In catheter 40, the surface of end portion 84 of the fiber optic is scoured or abraded back from fiber optic end 80 a distance A of about 5 centimeters. Light transmitted along the fiber optic 72 from end 78 is reflected internally until it reaches the portion 84 and is then emitted circumferentially along the length of the portion. The intensity of the emitted light increases from portion end 86 to tip 82.

While the catheter apparatus 10, 26 and 40 illustrated herein may be used for a number of applications, they are primarily intended for urinary tract illumination and drainage. In such applications the flexible catheter tubes 16, 27 and 42 may have a length of approximately 15 cm. and a diameter of approximately 20 French or 6.6 mm. The drainage openings communicating the lumen with the exterior of the catheter tube may be located approximately 1 cm. from the distal end of the tube.

In all three embodiments of the invention a resilient rubber drainage adapter is secured to the proximal end of a flexible transparent catheter tube. The drainage adapters include axially aligned major and minor aperatures with the major aperature forming a fluid tight resilient joint on the proximal end of the catheter tube and with a flexible light transmitting fiber optic member extending through the minor aperature and into and along the catheter tube so that the free end of the fiber optic is adjacent the distal end of the tube. The position of the fiber optic in the tube may be adjusted by sliding the fiber optic back and forth with respect to the drainage adapter. In the case of the embodiments of FIGS. 1 and 4, the fiber optic is located freely within the lumen of the tube. The flexibility of the fiber optic and tube facilitate insertion and use of the apparatus.

In describing the use of the catheter apparatus disclosed herein, reference will be made to catheter apparatus 40 of FIG. 4, but it will be appreciated that the embodiments of FIGS. 1 and 3 may be used in exactly the same manner and that the description will equally well apply to all three embodiments. The catheter apparatus are inexpensive to manufacture and may be sterilized and sealed within packages following manufacture. In this way, the catheter apparatus are available for use in a sterile package. Because they are low cost, the catheter may be discarded following use.

The luminating catheters disclosed herein are primarily intended to illuminate the urethra and bladder of a female patient during an open surgical procedure to correct stress incontinence. In this procedure the distal end of the catheter tube is inserted through the urethra and into the bladder of the patient with the free end 44 of the catheter tube located centrally within the bladder so that urine is drained through the eyelets, into and along the lumen of a catheter, through the drainage adapter and drainage funnel and into a collecting bag attached to the leg of the patient. The inlet areas of the eyelets and the interior cross section of the lumen passage or passages is sufficient to provide desired drainage of the bladder.

FIG. 7 is a representational view illustrating the distal end 44 of catheter tube 42 extending into bladder B. The diameter of the tube 42 of FIG. 4 and of the tubes of the apparatus of FIGS. 1 and 3 is approximately 20 French so as to provide a close, snug fit with the internal wall of the urethra C. In this way, the catheter tube is fixed in the urinary tract so that the position of the light emitting end 84 of the fiber optic is fixed and movement of the light emitting end 84 with respect to the tube moves the end with respect to the tract. In some patients it may be desirable to use slightly different diameter tubes in order to assure the desired snug fit.

After the surgeon has opened the abdominal cavity to expose the bladder and the catheter is in place as illustrated in FIG. 7 with the adapter 76 secured to a high intensity light source and aperature 66 attached to a collecting bag, the light transmitted along the fiber optic 72 radiates circumferentially outwardly along the abraded or scored end portion 84 for a distance A. The surgeon may then adjust the axial position of the fiber optic within the catheter tube to position the source of light within the urinary tract as desired. For a given application, it may be desirable that the light emitting portion of the fiber optic be located nearly entirely within the body of the bladder so that the light illuminates the walls of the bladder to enable the surgeon to positively locate the bladder by sight. In other situations, it may be desirable to withdraw the fiber optic member slightly as illustrated in FIG. 7 so that the proximal end of the light emitting portion A is partially located within the urethra C of the patient and the light illuminates both the walls of the bladder, the bladder-urethral junction and the urethra. In this situation, a higher intensity of light is required to illuminate the urethra and bladder-urethra junction than is required to illuminate the walls of the bladder. The intensity of the light emitted from the fiber optic is greatest at the proximal end of abraded portion 84 nearest the light source so that the required high intensity light is provided to illuminate the urethra and the urethral-bladder junction.

Internal cold illumination of this type enables the surgeon to locate the structure of the urinary tract visually, without deforming the tract and is particularly desirable where correct performance of a surgical, diagnostic or other procedure requires exact location of the urethra and its junction with the bladder. FIG. 7 illustrates the use of a catheter device according to the invention in performing the Marshall-Marchetti-Kranz procedure on a female patient to surgically correct stress incontinence resulting from an overly large urethrovesical angle. FIG. 5 illustrates a bladder D where the urethra E extends above bladder at a large posterior urethrovesical angle of 120°. In constrast, FIG. 6 illustrates a bladder F with a urethra G extending therefrom at a normal posterior urethrovesical angle. The angle of FIG. 5 may be the result of weakened abdominal muscles. The patients having increased urethrovesical angles in this order of 120° are subject to stress incontinence.

The Marshall-Marchetti-Kranz procedure for restoring the conventional urethrovesical angle as shown in FIG. 6 requires placement of a number of primary suspension sutures H at the urethrovesical junction and through the periosteum of the pubus H or, if feasible, into the cartilage of the symphysis.

The medical profession recognizes the success of the Marshall-Marchetti-Kranz procedure depends upon proper location of the primary suspension sutures at the urethrovesical junction. Improper location of the sutures outwardly of the junction reduces the change in the urethrovesical angle while improper location of the sutures inwardly of the junction risks hematuria, urinary extravasation, bladder calculi, ureteral and urethral legations, and suture fixation of conventional drainage catheters.

In performing this procedure it is essential that the sutures be placed at the urethrovesical junction. The catheter apparatus disclosed herein enables the surgeon to see the surface of the bladder, the junction with the urethra and the urethra thereby providing the surgeon with ability to locate the suspension sutures exactly as required by the procedure without injury to the patient. The sutures may be accurately and quickly placed in order to insure the success of the procedure and reduce operative time.

The high intensity light transmitted from the abraded portion of the fiber optic member is cool so that it does not injure the surrounding tissue. Additionally, in catheter apparatus 40, the drainage funnel 62 extends away from the drainage adapter 56 generally parallel to the axis of the fiber optic member. This facilitates the location of the drainage bag at an accessible location remote from the incision.

Prior to our invention it has been conventional to locate the urethrovesical junction by endoscopy, cystotomy or manual palpation of the vesical neck following insertion of a catheter and inflation of a balloon within the bladder. In extreme cases, traction has been applied to the catheter to aid in location of the junction. These procedures are, at best, imprecise and distort the urinary tract.

In contrast with the standard procedure for locating the urethrovesical junction, our invention illuminates the undistorted bladder junction and urethra to provide the surgeon a readily apparent visual indication of the surrounding tissue. Our catheter apparatus 40 shown in FIG. 4 has been used in 18 primary Marshall-Marchetti-Kranz procedures for femal stress incontinence with a 100% success rate. The patients have not experienced postoperative stress incontinence and there has been no immediate or delayed surgical morbidity as a result of the procedure.

While we have illustrated and described embodiments of our invention, it is understood that these are capable of modification and use in applications other than those referred to herein. Therefore, we do not wish to be limited to the precise details asset forth but desire to avail ourselves of such changes and alterations as fall within the purview of the following claims.

What we claim is our invention:

1. An illuminated drainage catheter including a flexible transparent catheter tube having distal and proximal ends and an internal drainage lumen extending the length thereof and open at the proximal end of the tube and at or adjacent the distal end of the tube; a drainage adapter having an internal collecting portion with major and minor axially aligned aperatures located on opposite sides of said portion, and drainage member extending laterally of said axis including an aperature at the free end thereof adapted to be connected to a liquid drainage receptacle and a passage extending from the collecting portion to such aperature; a fiber optic member including an elongate flexible light transmitting fiber optic having proximal and distal ends, a light emitting surface extending around the circumference of a length of the fiber optic adjacent the distal end thereof, a mounting member on the proximal end of the fiber optic for attachment to a light source whereby light from the source is transmitted to the fiber optic, along the fiber optic and is emitted from the area of light transmitting surface radially outwardly of the fiber optic, a fluid tight connection joining the proximal end of the catheter tube to the major aperature of the drainage adapter; the proximal end and mounting member of the fiber optic member being located outwardly of the catheter tube and drainage adapter with the fiber optic extending therefrom through the minor aperature, the internal collecting portion and major aperature of the drainage adapter and into and along the interior of the catheter tube with the distal end of the fiber optic located adjacent the distal end of the tube and the light transmitting surface extending along a length of the tube; the interior surface of the minor aperature resiliently engaging the exterior surface of the fiber optic to form a fluid tight sliding joint therebetween thereby the fiber optic may be axially moved with respect to the minor aperature to move the light transmitting surface along the catheter tube to a desired location while maintaining a fluid tight seal between the fiber optic and the minor aperature so that liquid flowing along the lumen is discharged through the drainage member.

2. An illuminated drainage catheter as in claim 1 wherein said drainage member is formed from an integral body of resilient material and the proximal end of the catheter tube is resiliently confined within said major aperature.

3. An illuminated drainage catheter as in claim 2 wherein the cross sectional area of the lumen is greater than the cross sectional area of the fiber optic and the fiber optic extends along the lumen.

4. An illuminated drainage catheter as in claim 3 wherein the distal end of the catheter tube is sealed and including at least one drainage opening extending through the wall of the catheter tube adjacent the sealed distal end.

5. An illuminated drainage catheter as in claim 3 wherein the free end of the drainage member extends away from the major aperature in a direction essentially parallel to the axis between the aligned aperatures.

6. An illuminated drainage catheter as in claim 5 wherein said fiber optic member includes an insulating sheath surrounding the fiber optic and extending from the mounting member a distance along the fiber optic towards the drainage adapter, the fiber optic being free of said sheath for a distance from the distal end equal to or greater than the distance from the distal end of the catheter tube to the minor aperature of the drainage adapter whereby the position of the light transmitting surface may be moved to different locations within the catheter tube.

7. An illuminated drainage catheter as in claim 3 wherein the light transmitting surface is abraded and the intensity of light emitted circumferentially from such surface decreases from the proximal end of the surface to the distal end of the surface.

8. An illuminated drainage catheter as in claim 7 wherein the outer diameter of the catheter tube is about 20 French.

9. An illuminated drainage catheter as in claim 7 wherein the length of the light emitting surface along the fiber optic is approximately 5 cm.

10. An illuminated drainage catheter as in claim 7 wherein the distal end of the light emitting surface is located at the distal end of the fiber optic.

* * * * *

UNITED STATES PATENT OFFICE
CERTIFICATE OF CORRECTION

PATENT NO. : 4,248,214

DATED : February 3, 1981

INVENTOR(S) : Richard E. Hannah
Robert S. Kish

It is certified that error appears in the above-identified patent and that said Letters Patent are hereby corrected as shown below:

Column 1, line 39 change "comprise" to --comprises--; and, line 45 after "includes" insert --a--.

Column 2, lines 53 and 55 change "diagramatic" to --diagrammatic--.

Column 5, line 22 change "bar" to --area--; and line 36 change "9" to --is--.

Column 6, line 67 (last line) change "catheter" to --catheters--.

Column 7, line 66 change "above" to --from--.

Column 8, line 54 change "femal" to --female--.

Claim 1, line 7 after "and" insert --a--.

Signed and Sealed this

Nineteenth Day of May 1981

[SEAL]

Attest:

RENE D. TEGTMEYER

Attesting Officer          Acting Commissioner of Patents and Trademarks